United States Patent [19]

Sessions et al.

[11] 4,130,119
[45] Dec. 19, 1978

[54] OCCLUSION DEVICE

[75] Inventors: Robert W. Sessions, Hinsdale; Jerome Jeslis, Chicago; Richard A. Rodzen, Bolingbrook, all of Ill.

[73] Assignee: Barlow Mfg. Corp., Hinsdale, Ill.

[21] Appl. No.: 783,839

[22] Filed: Apr. 1, 1977

[51] Int. Cl.² ............................................. A61M 25/00
[52] U.S. Cl. ...................................... 128/325; 128/348
[58] Field of Search .................... 128/325, 348, 349 B, 128/349 BV, 350 R, 351, 344, 246, 1 R; 138/43

[56] References Cited

U.S. PATENT DOCUMENTS

| 3,795,246 | 3/1974 | Sturgeon | 128/325 |
| 3,812,841 | 5/1974 | Isaacson | 128/1 R |
| 3,834,394 | 9/1974 | Hunter et al. | 128/325 |
| 3,923,065 | 12/1975 | Nozick et al. | 128/348 |

Primary Examiner—Dalton L. Truluck
Attorney, Agent, or Firm—Hill, Gross, Simpson, Van Santen, Steadman, Chiara & Simpson

[57] ABSTRACT

A device for occluding a fluid passageway such as a blood vessel, particularly a human blood vessel, which is of the balloon type, adapted to be inserted, by means of a catheter structure, into a blood vessel and moved thereby to the desired point of occlusion, at which the ballon is expanded by means of a fluid conducted through the catheter, thereby firmly securing the occlusion device to the vessel side wall. Novel means are provided, including a dual valve mechanism for insuring the retention of the expanding fluid in the device, thereby providing efficient sealing of the balloon to substantially eliminate the possibility of fluid leakage upon separation of the occluding device from the inserting catheter structure. The invention also provides novel means for insuring firm attachment of the occlusion device to the adjacent end of the catheter structure, which prevents an undesired inadvertent separation between the occluding device and the catheter until the occluding operation is completed, with such results being achieved by utilization of the fluid conducting needle as a locking element of the connection and at the same time the actuating element for opening the valves of the occluding device.

12 Claims, 3 Drawing Figures

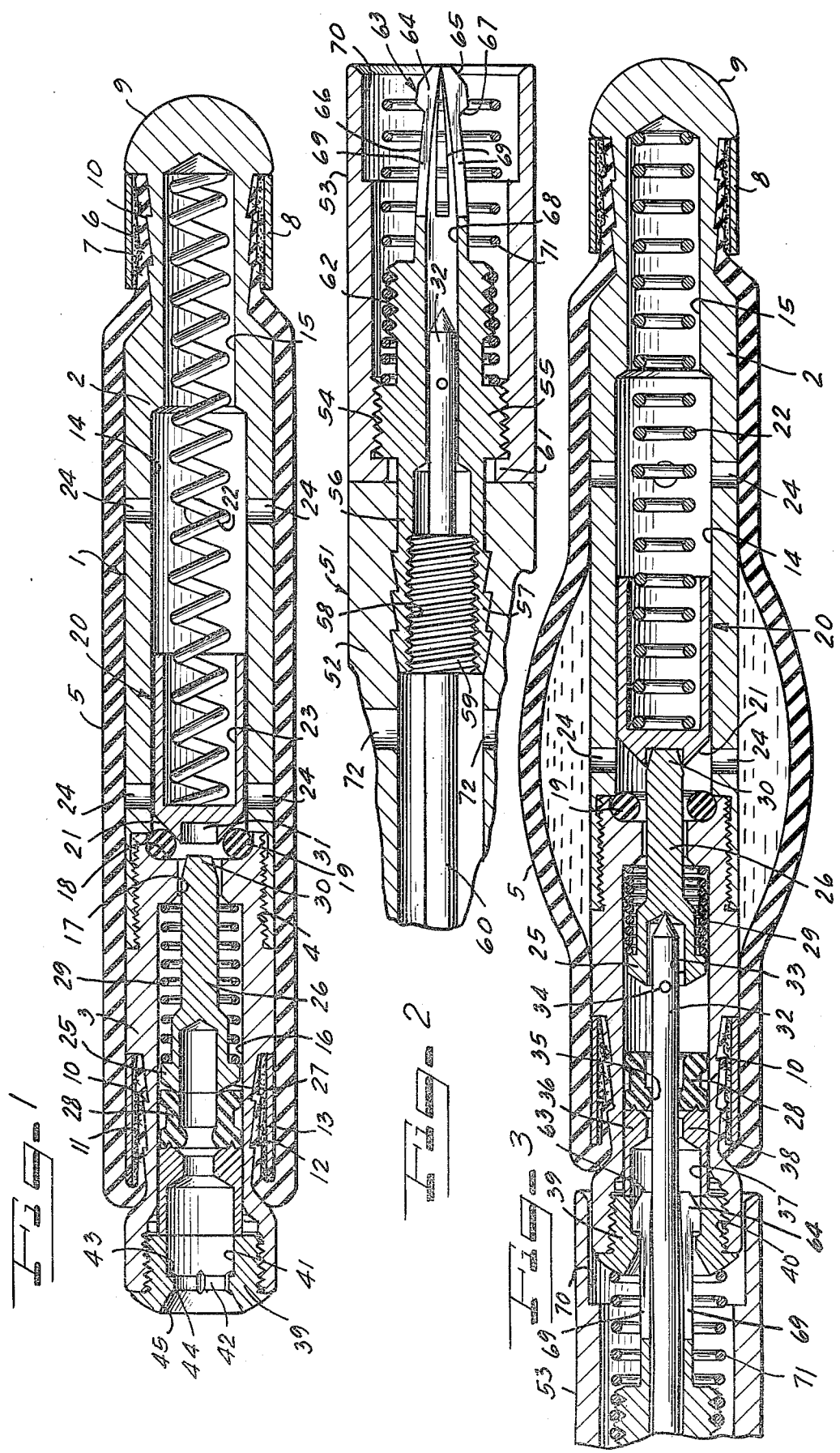

OCCLUSION DEVICE

BACKGROUND OF THE INVENTION

The present invention relates to an occluding device, adapted to be inserted in a blood vessel or the like by means of a catheter structure, which carries the occluding device at its distal end, with such occluding device being detachably supported by the catheter structure. Occluding devices of the balloon type have an expandable portion, which may be expanded from its retracted condition by means of the reception therein of a fluid therein, which is supplied through the catheter and, upon completion of the expansion operation, the catheter is detached from the occluding device and withdrawn from the blood vessel, with the occluding device remaining therein to perform the desired function.

The present invention is an improvement in devices of this type illustrated in prior U.S. Pat. No. 3,834,394 granted to James Hunter and Robert Sessions on Sept. 10, 1974. Extensive studies and tests with devices such as illustrated in such patent have established the need, in addition to other desirable characteristics, for maximum safety with respect to leakage of fluid from an inserted occlusion device and undesired deflation of the occlusion device. An occlusion device such as the type here involved will in a matter of a relatively short period of time, for example, several weeks following insertion, be substantially permanently retained at the desired location in the blood vessel, whereby deflation thereafter would have no disadvantageous effect. Tests have shown that regardless of the type of material employed in the balloon structure after a prolonged period of time, following insertion, the liquid in the balloon will eventually pass through the material of the balloon and enter the blood stream permitting the balloon to collapse. However, should a leakage take place, for example through the sealing valve mechanism of the occlusion device prior to such ultimate natural retention in the blood vessel, it would be possible for the occlusion device to travel in the blood vessel with possible serious consequences. It is therefore of extreme importance that the occluding device be of a construction that substantially completely precludes leakage in the valve mechanism associated therewith.

It also is of importance that the connection between the occluding device and the adjacent end of the catheter structure be such that the connection is completely foolproof with respect to inadvertent disconnection during the insertion operation and during the expanding operation so that the occlusion device cannot be lost from the end of the inserting catheter. At the same time, while the construction must be such that a positive and foolproof interlock is achieved, such construction also must have the corresponding feature of a sure and foolproof release action that precludes the possibility of the occluding device tending to remain attached to the catheter and thus defeating the desired purpose.

The desired efficiency and safety, with respect to the valve mechanism of the occlusion device, is achieved in the present invention by the utilization of dual successive valve structures, either of which is sufficient to provide the desired sealing action, and in which the primary valve mechanism retaining the liquid in the balloon may be of relatively heavy duty construction providing maximum sealing efficiency. The construction is such that a fluid conducting needle of the catheter may be inserted into the occlusion device to effect a positive actuation of both valve structures and simultaneously providing the safety feature that, in the absence of the proper connection of the catheter with the occlusion device, the valve structures will remain in a closed position.

The invention also is directed to a novel connecting structure between the occluding device and the adjacent distal end of the catheter structure in which the latter is provided with a collet-like head structure which is radially expandable and contractable, and which, in contracted position, is adapted to be inserted into a receiving socket provided on the proximal end of the occluding device. The fluid supply needle of the catheter, which is axially extendable from and retractable into the distal end of the catheter may then be moved to its extended position operative to effect expansion of the head into a firm, positive engagement with the socket of the occluding device, thereby preventing separation between the two, with continued extension of the needle being operable to actuate and open the valve members of the occluding device.

In use, the occluding device would be attached to the catheter structure with the catheter needle locking the elements in assembled relation, at which time the needle may be fully extended to open the valve members, and with the structure in such condition it may be inserted into the blood vessel and the occlusion device position at the desired location therein. Liquid may then be supplied through the needle to the occlusion device under sufficient pressure to provide the desired expansion of the balloon structure. The needle is then fully retracted into the catheter tube permitting the collet head to contract, whereby it may be freely withdrawn from the occlusion device by a withdrawal movement of the catheter. To assist such action, resilient means may be provided in the distal end of the catheter, operative to exert force on the socket of the occlusion device in a separating direction, whereby upon withdrawal of the needle and contraction of the collet head, such forces will provide additional separating force between the occluding device and the distal end of the catheter.

The invention further has among its objects the production of an occluding device which, in spite of its relatively extremely small size is very durable, providing excellent sealing action of the expanding liquid, and at the same time a relative simplicity in its design and production.

BRIEF DESCRIPTION OF THE DRAWINGS

In the drawings wherein like reference characters indicate like or corresponding parts:

FIG. 1 is a longitudinal or axial section through an occlusion device constructed in accordance with the present invention;

FIG. 2 is a similar longitidunal or axial sectional view of the distal end of a catheter adapted to effect insertion of the occlusion device of FIG. 1; and FIG. 3 is a similar sectional view of the structures of FIGS. 1 and 2 illustrating the same in assembled relation, with the balloon in an expanded position.

DETAILED DESCRIPTION OF THE INVENTION

The Occluding Device

Referring to FIG. 1, the occluding device illustrated comprises a rigid body indicated generally by the reference numeral 1, constructed from suitable material as for example stainless steel and illustrated as being constructed into two sections, a distal or leading section and a proximal or trailing section 3, suitably rigidly secured together as for example by means of a threaded connection 4, illustrated as comprising external threads formed on the adjacent end of the proximal portion 3 and internal threads formed on the cooperable end of the portion 2. Encircling the body 1 is an expandable sleeve 5 constructed, for example, of latex with its respective ends being secured to the body 1 in fluid-tight relation.

As illustrated, the distal portion 2 is provided with an annular channel or groove 6, in which the adjacent end of the sleeve 5 is disposed and firmly secured thereto by a wrapping 7 of suture material or the like which, in the embodiment illustrated, is further overlaid by a sleeve 8 of metal or other suitable material. In the construction illustrated, the free distal end of the portion 2 is semispherical as indicated at 9, the curvature of which merges with the cylindrical configuration of the sleeve 8. The bottom wall 10 of the channel 6, may be provided with a bottom wall of generally serrated configuration in longitudinal section, to firmly retain the sleeve end thereon.

In like manner the proximal portion 3 is provided with an annular channel or recess 11 of reduced diameter in which is disposed the adjacent proximal end of the sleeve 5 which is likewise secured to the body portion by a suture wrapping 12 and a sleeve 13 of metal or the like, with the recess 11 having a bottom wall 10 of serrated configuration to provide a firm engagement of the sleeve and body portion. It will be noted that in this case the sleeve member may be brought around over the secured end of the sleeve.

The hollow distal portion 2 is provided with a relatively large diameter bore 14 and an axially aligned smaller bore 15 disposed at the distal end of such portion. In like manner, the proximal portion 3 is provided with a relatively large diameter bore 16 and a smaller bore 17 which connects the bore 16 with the bore 14 of the portion 2. The distal end of the bore 17 terminates in an enlarged counter bore 18 forming a seat for an O-ring 19, cooperable with a valve member, indicated generally by the numeral 20, which is axially movable in the bore 14 and provided with a valve seat 21, of conical configuration, adapted to engage the O-ring 19 and thereby effect a seal between the bore 14 and the bore 17. The valve member 20, which may be termed a "plug shuttle", is urged into sealing engagement with the O-ring 19 by a coiled compression spring 22, the proximal end of which is disposed within the bore 23 of the valve member 20, while the distal end of which is seated on the bottom of the bore 15. The portion 2 is provided with a plurality of generally radially extending ports 24 in the side wall of the portion which provide communication between the bore 14 and the interior of the balloon sleeve 5.

Slidably movable in the bore 16 is a second valve member 25, which may be termed a "stemmed shuttle", provided at its distal end with an elongated stem 26 which extends into the bore 17, and at its proximal end with a generally conical valve seat 27 adapted to engage a resilient ring member 28, under the action of a coil compression spring 29 to provide a further seal between the exterior of the hollow body 1 and the interior of the bores 16 and 17.

The distal end 30 of the stem 26 is adapted, upon inward movement of the stemmed shuttle to enter a recess 31 in the plug shuttle 20 and thereat engage the latter, with continued inward movement of the stemmed shuttle 25 being operative to move the plug shuttle 20 in the same direction, in opposition to the spring 22, to disengage the plug shuttle from the O-ring 19 and thereby open the interior of the body with respect to the exterior thereof.

As illustrated in FIG. 3, the plug and stemmed shuttles 20 and 25 are adapted to be moved to their open positions by means of a hollow needle 32 which also provides ingress for the liquid, by means of which balloon sleeve 5 is to be expanded. The stemmed shuttle 25 is provided with a bore 33 in its proximal end of a size to comfortably receive the free end of the needle 32 with the latter being provided with one or more ports 34 therein through which liquid may be discharged from the needle into the bore 17, around the open plug shuttle 20 and into the bore 14 for discharge through the ports 24 into the interior of the balloon sleeve 5 to effect an expansion thereof as illustrated in FIG. 3. The sealing ring 28 is generally tubular in shape and is provided at its proximal end with a radially inwardly extending needle-engaging flange 35 adapted to effect a fluid-tight seal between the needle and the exterior of the body portion, to thereby prevent liquid flow out of the structure during the expansion operation. Such proximal end of the sealing ring 28 is adapted to bear on the adjacent distal end of a tubular needle guide sleeve 36 having a relatively large bore 37 at its proximal end and provided at its distal end with a radially inwardly directed annular flange portion 38 which forms guide means for the needle 32 when inserted in the body 1.

Outward movement of the needle guide 36 is prevented by a retainer ring which is secured to the adjacent proximal end of the body portion 3 by cooperable threads 40. The retainer ring 39 is provided with a bore 41 which in the embodiment illustrated is of the same diameter as the bore 37 in the needle guide ring 36, with the bore 41 communicating with the exterior through a restricted bore 42 forming a shoulder 43 at the junction of the two bores. The bore 42 may also be provided with a plurality of notches 44, adapted to be engaged by a tool of polygonal cross section, by means of which the retainer ring may be firmly secured to the body portion 3 with the bore 42 terminating at the free end of the ring 39 in a flared mouth 45.

The Catheter Connecting Structure

FIG. 2 illustrates in section the cooperable end of a catheter, indicated generally by the numeral 51, which comprises a flexible tubing 52, for example of tygon, with the free end of the catheter terminating in an adapter sleeve 53 rigidly secured, by means of threads 54, to a generally cylindrically shaped elongated member 55, hereinafter termed the "adapter collet", which is provided with a shank portion 56 having external rings 57 of generally serrated configuration in longigudinal cross-section which upon a forced insertion of the shank portion 56 into the bore of the tube 52 will result in a firm connection between the two. The shank portion 56 is provided with internal threads 58 which mate with the threaded head 59 of a hollow tube 60 having an internal diameter of a size to slidably receive the needle 32. The opposite ends of the tubing 52 and metal tube 60 are suitably secured to a handle portion which also may include means for reciprocating the needle 32 in the tube 60.

As will be apparent from FIG. 2, the sleeve 50 is threaded on the member 55 from the proximal end of the latter, with the sleeve being rotated until the inwardly directed flange 61, at the proximal end of the sleeve, firmly engages the adjacent shoulder on the member 55 at the junction of the threaded portion 54 with the shank portion 56. Preferably, the construction of the handle end of the catheter is such that by effecting relative movement of the tube 60 with respect to the tubing 52 the latter may be placed under a suitable degree of compression, thus firmly seating the free end edge of the tubing on the adjacent external face of the flange 61 of the sleeve 53.

The opposite or distal end of the member 55 is provided with a second threaded portion 62 and terminates in an adapter collet structure, designated generally the numeral 63, which is provided at its extreme free end with a head portion 64, having a generally conical shaped end 65, with the head being carried by a relatively narrow neck portion 66 to form a retaining shoulder 67 at the proximal end of the head 64. The member 55 is provided with a needle receiving bore 68 therein which extends through the neck portion 66, the latter being provided with a plurality of slots 69 therein dividing the head 64 into a plurality of segments which, as illustrated in FIG. 2, are suitably bent or otherwise so formed that they normally assume the positions illustrated in FIG. 2 with the head 64 thereby being contracted to a reduced diameter which is less in size than the diameter of the entrance bore 42. The respective head segments are sufficiently resilient that upon extension of the needle 32 through the bore 68, as illustraged in FIG. 3, the head segments will be expanded to an external diameter approximately matching the diameter of the bore 41 of the retainer ring 39, thereby locking the shoulders 67 of the head segments with the cooperable annular shoulder 43 on the retaining ring 39.

It will be appreciated that the needle 32 not only serves as the actuating means for engaging the head 64 with the retaining ring 39, but also serves as an interlock for the assembly, as it is impossible for the head segments 64 to contract to a position permitting withdrawal through the bore 42, as long as the needle extends through the bore 68. Consequently, inadvertent disconnection of the catheter from the body 1 is impossible while the inflation of the balloon is taking place. As illustrated, the free end of the sleeve 53 is provided with a counterbore 70 of a diameter sufficiently greater than the external diameter of the adjacent proximal end of the body portion 3 to permit ready insertion of such end of the body member into the sleeve as illustrated in FIG. 3.

When it is desired to disconnect the catheter structure from the body, the needle 32 is withdrawn into the catheter to a position, such as illustrated in FIG. 2 permitting the head segments 64 to contract to the position illustrated in FIG. 2 enabling withdrawal thereof from the retaining ring 39. To insure immediate separation of the catheter end from the occlusion member, following expansion of the balloon and withdrawal of the needle 32, disposed in the sleeve 53 is a compression spring 71 having its inner end threaded upon the threaded portion 62 of the member 55 and its outer end disposed in the counterbore 70, adapted to engage the adjacent end of the retaining ring 39 thereby urging the shoulders on the retaining ring and on the head of the collet into engagement, and upon withdrawal of the needle 32 into the member 55, and contraction of the head 64, the spring 71 will apply separating forces between the end of the catheter and the adjacent end of the occlusion device to effect a speedy and efficient withdrawal of the collet head from the retaining ring 39 and disconnection of the catheter from the occlusion device.

Assembly

The entire structure with the exception of the balloon sleeve 5 may be assembled, with the spring 29, stemmed shuttle 25, sealing ring 28, needle guide ring 36 and retaining ring 39 being assembled in the proximal body portion 3 in that order and the retaining ring 39 turned down tight on the adjacent end of the body by means of a suitable tool inserted in the bore 42 and engaged with the notches 44 therein as previously described.

The O-ring is seated in operative position in the opposite end of the body portion 3 and the body portion 2 with assembled spring 22 and plug shuttle 20 inserted therein, is secured to the body portion 3 by means of the threads 4. It will be appreciated that torque may be applied between the body portion 2 and the body portion 3, as well as between the retaining ring 39 by means of the previously mentioned tool inserted in the bore 42 and a suitable cooperable tool inserted in bores 24 in the body portion 2. Thus, by applying torque between the body portion 2 and the retaining ring 39, all of the threaded parts may be firmly secured together.

Following assembly of all of the body components, the balloon sleeve 5 may be everted and the proximal end of the body portion inserted in the adjacent end of the sleeve member until the end edge thereof abuts the shoulder formed at the distal end of the serrated portion 11. A suture wrapping 12 is applied which is followed, in the embodiments illustrated, by a clamp ring 13. As previously mentioned, the ring 13 may be omitted and the sleeve adequately affixed to the body portion merely by an adequate amount of suture wrapping. The balloon sleeve is then drawn back over the body, i.e., turned right side out, into the position illustrated in FIG. 1, and the free end secured to the body portion 3 by suture winding 7 and clamping band 8, merely adequate suture wrappings being employed if so desired.

As previously generally described, the adjacent end of the catheter is assembled by initially screwing the sleeve 53 onto the member 55 after which the threaded head of the tube 60 is firmly screwed into the threads 25 on the shank 56, the tubing 52 threaded over the tube 60 and worked over the serrated shank 56 to the position illustrated in FIG. 2. As previously mentioned, preferably compression forces are exerted on the tube 52 by means of the tube 60 to provide a firm joint between the adjacent end of the sleeve 53 and the end of the tubing 52. The spring 71 normally will be mounted on the threaded portion 62 prior to the assembly of the sleeve 53 therewith.

Operation

General medical techniques involved in the insertion of the occlusion device in a blood vessel will follow the explanation presented in the prior patent, previously referred to, with the occlusion device initially being mounted on the end of the catheter by inserting the distal end of the occlusion device, comprising the corresponding end of the body portion 3 and retaining ring 39, into the bore 70 of the adapter sleeve 53 of the catheter, engaging the end of the ring 39 with the free end of the spring 71 and compressing the latter until the collet head 64 has fully entered the bore 41-37, substantially as illustrated in FIG. 3. While retaining the relative positions of the members, the needle 32 is then advanced to extend the needle into the body and thus expand the collet head 64, securely locking the catheter and occlusion device to one another. The needle is then further extended to a position substantially as illustrated in FIG. 3 with the free end of the needle entering the bore 33 and engaging the bottom thereof, forcing the stemmed shuttle 25 in opposition to the spring 29, toward the distal end of the device, with the free end 30 entering the recess 31 in the plug shuttle 20, engaging the latter and moving the same toward the distal end of the device in opposition to the spring 22. Following insertion of the catheter and occlusion device in the blood vessel, the passage of which, as discussed in the previous patent, may be monitored by use of a suitable dye supplied through the catheter in the space between the tubing 52 and tube 60 and discharge through the openings 72 in the tubing side wall, fluid is supplied through the needle into the body 1, passing around the stemmed shuttle 25, past the O-ring 19 and through the ports 24 into the interior of the balloon sleeve, to expand the latter, an expansion thereof being illustrated in FIG. 3.

When the balloon has been adequately expanded, the needle 32 is withdrawn from the occlusion device and after being sufficiently retracted into the catheter will permit the collet head 64 to contract to its original position, permitting its withdrawal through the bore 42, with separating movement being urged by the compression spring 71. Following disconnection of the occlusion device the catheter may be withdrawn from the blood vessel.

It will be particularly noted from the above description, that in the invention the occlusion device is positively locked to the end of the catheter structure and as long as the needle is in its extended position, as can be readily insured from the handle end of the device, there is no danger of undesired separation of the occlusion device from the end of the catheter. Likewise, it will be apparent that as the valve members are opened by mechanical action of the needle, as distinguished from liquid pressure of the expanding liquid, a relatively heavy spring can be utilized particularly for the spring 22 associated with the plug shuttle 20 to insure a very effective seal of the expanded balloon. Likewise, by use of the double valve system maximum protection is afforded against leakage from the device following expansion.

It will be further noted that the sealing ring 28 serves the double purpose of effecting a seal between the body portion 3 and the stem shuttle 25 as well as an effective seal between the body and the inserted needle 32, preventing any leakage of liquid under pressure during the expanding of the balloon. In like manner the plug shuttle 20 effects a seal between the body portion 3 and the body portion 2 with the junction between the body portions 2 and 3 being at the same side, i.e., the distal side of the O-ring 19 so that the threaded joint between the two body portions need not necessarily form a fluid-tight seal.

Having thus described our invention, it will be obvious that although various minor modifications might be suggested by those versed in the art, it should be understood that we wish to embody within the scope of the patent granted hereon all such modifications as reasonably, and properly come within the scope of our contribution to the art.

We claim as our invention:

1. A device for effecting occlusion of a blood vessel, in the form of an expandable balloon-type structure, comprising an elongated hollow, rigid body, closed at its distal end and open at its proximal end, a deformable balloon sleeve encircling the intermediate portion of and secured, at its ends, to the body in fluid-tight relation, the body having at least one opening therein connecting the hollow interior thereof with the balloon interior, a first valve member disposed in said body, adjacent the distal end thereof, and movable relative thereto, said valve member having a needle-engaging portion and a sealing portion, sealing means cooperable with said sealing portion to provide a seal between the interior of said hollow body and the exterior thereof, and spring means engageable with said valve member and a portion of the body for urging said valve member into sealing engagement with said sealing means, a second valve member, movable relative to, and disposed in said body between said first valve member and said opening to the balloon interior, said first valve member being movable relative to said second valve member, second sealing means operatively disposed between the inner end of said first valve member and the second valve member, said second valve member having a sealing portion cooperable with said second sealing means to provide a seal between said second valve member and said body, further spring means engageable with said second valve member and a portion of said body for urging said second valve member into sealing engagement with said second sealing means, such valve structures thus being operatively connected in series for cooperably providing connection between the balloon interior and open end of said body, said first valve means being engageable, upon movement thereof in opening direction, with said second valve member to move the latter in opening direction, whereby both valve members may be in open position, means at the open end of said body for guiding a hollow fluid supply needle into said body for engagement with said first valve member to move the latter in opening direction, and means carried by said body for effecting a fluid-tight seal between the open end of said body and such an inserted supply needle.

2. A device according to claim 1, wherein the first-mentioned sealing means is disposed in the proximal body member and the second sealing means is disposed in said proximal body member adjacent the inner end thereof, whereby a seal may be effected between said second valve member and said proximal body member.

3. A device according to claim 1, wherein said first-mentioned sealing means is provided with a portion engageable with said valve means for effecting a seal thereof, and is further provided with a needle-engaging portion forming the means for sealing an inserted needle.

4. A device according to claim 3, wherein said first-mentioned sealing means is in the form of a ring, said sealing ring and said needle-sealing means being constructed as a single unitary member.

5. A device according to claim 1, comprising in further combination, means disposed at the open end side of said needle guiding means for detachable engagement with cooperable means associated with such a supply needle for retaining the latter in operable position relative to said body.

6. A device according to claim 5, wherein said means at the open end side of said needle guiding means comprises an inwardly directed shoulder forming said needle guiding means adapted to be engaged by shoulder means on such cooperable means associated with such a supply needle.

7. A device according to claim 1, wherein said first-mentioned spring means comprising an elongated compression spring having one end engageable with said body and the other end with the sealing portion of said first-mentioned valve member.

8. A device according to claim 7, wherein said needle engaging portion and said sealing portion of said first-mentioned valve member are rigidly connected to form a single unitary structure.

9. A device according to claim 7, wherein said sealing portion of said first-mentioned valve member and cooperable sealing means are disposed at the inner end of said needle engaging portion.

10. A device according to claim 1, wherein said second sealing means comprises an O-ring.

11. A device according to claim 1, wherein said body is constructed in the form of two individual body members rigidly connectible, with one forming the distal portion and the other the proximal portion of the device, the distal end of the balloon being secured to the distal body member and the proximal end of the balloon being secured to the proximal member, the first valve member and associated spring means being movably disposed in the proximal body member and the second valve member and associated spring means being movably disposed in the distal body member.

12. A device according to claim 11, wherein the first-mentioned sealing means is disposed in the proximal body member and the second sealing ring is disposed in said proximal body member adjacent the inner end thereof, whereby a seal may be effected between said second valve member and said proximal body member.

* * * * *